US009427405B2

(12) United States Patent
Masserini et al.

(10) Patent No.: US 9,427,405 B2
(45) Date of Patent: Aug. 30, 2016

(54) LIPOSOMES CAPABLE OF EFFECTIVELY BINDING THE BETA AMYLOID PEPTIDE

(75) Inventors: Massimo Masserini, Santa Margherita Ligure (IT); Francesca Re, Busto Garolfo (IT); Maria Silvia Sesana, Merate (IT)

(73) Assignee: Universita degli Studi de Milano-Bicocca (IT)

( * ) Notice: Subject to any disclaimer, the term of this patent is extended or adjusted under 35 U.S.C. 154(b) by 414 days.

(21) Appl. No.: 12/997,079

(22) PCT Filed: Jun. 10, 2009

(86) PCT No.: PCT/IT2009/000251
§ 371 (c)(1),
(2), (4) Date: Feb. 28, 2011

(87) PCT Pub. No.: WO2009/150686
PCT Pub. Date: Dec. 17, 2009

(65) Prior Publication Data
US 2011/0177158 A1    Jul. 21, 2011

(30) Foreign Application Priority Data
Jun. 10, 2008  (IT) ............................... MI2008A1052

(51) Int. Cl.
*A61K 9/127* (2006.01)
*A61K 47/24* (2006.01)

(52) U.S. Cl.
CPC ............... *A61K 9/127* (2013.01); *A61K 47/24* (2013.01)

(58) Field of Classification Search
CPC ...................................................... A61K 9/127
USPC ........................................................... 424/450
See application file for complete search history.

(56) References Cited

U.S. PATENT DOCUMENTS

| | | | | |
|---|---|---|---|---|
| 5,814,335 | A * | 9/1998 | Webb et al. | 424/450 |
| 7,452,550 | B2 * | 11/2008 | Madden | A61K 9/0019 264/4.1 |
| 8,110,217 | B2 * | 2/2012 | Chancellor et al. | 424/450 |
| 2005/0064505 | A1 * | 3/2005 | Soto-Jara et al. | 435/7.1 |
| 2007/0031484 | A1 * | 2/2007 | Benz | A61K 9/127 424/450 |
| 2009/0306455 | A1 * | 12/2009 | Slade et al. | 600/12 |
| 2012/0021042 | A1 * | 1/2012 | Panzner et al. | 424/450 |

OTHER PUBLICATIONS

Sesana et al., "Membrane Features and Activity of GPI-Anchored Enzymes: Alkaline Phosphatase Reconstituted in Model Membranes", Biochemistry, vol. 47, No. 19, May 2008, pp. 5433-5440.
Re et al., "Prion Protein Structure is Affected by pH-Dependent Interaction with Membranes: A Study in a Model System", FEBS Letters, vol. 582, No. 2, Dec. 2007, pp. 215-220.
(Continued)

*Primary Examiner* — Gollamudi Kishore
(74) *Attorney, Agent, or Firm* — Akerman LLP

(57) ABSTRACT

Novel liposomes are described which are capable of effectively binding beta amyloid peptide and are useful for the treatment, prevention and diagnosis of Alzheimer's disease. Binding ability is provided by the presence in the formulation of particular natural lipids identified by the Applicant. These comprise a constant component, made up of cholesterol and sphingomyelin, and an additional variable component, made up of selected lipids.

12 Claims, 2 Drawing Sheets

2A

2B

(56) References Cited

OTHER PUBLICATIONS

Lin et al., "Kinetics and Enthalpy Measurements of interaction Between β-amyloid and Liposomes by Surface Plasmon Resonance and Isothermal Titration Microcalorimetry", Colloids and Surfaces B: Biointerfaces, vol. 58, No. 2, Jun. 2007, pp. 231-236.

Kazlauskaite et al., "Structural Changes of the Prion Protein in Lipid Membranes Leading to Aggregation and Fibrillization", Biochemistry, vol. 42, No. 11, Mar. 2003, pp. 3295-3304.

Harris, "In vitro Fibrillogenesis of the Amyloid β1-42 Peptide: Cholesterol Potentiation and Aspirin Inhibition", Micron, vol. 33, Nos. 7-8, Aug. 2002, pp. 609-626.

Chauhan e tal., "Interaction of Amyloid Beta-Protein with Anionic Phospholipids: Possible Involvement of Lys28 and C-Terminus Aliphatic Amino Acids", Neurochemical Research, vol. 25, No. 3, Mar. 2000, pp. 423-429.

Gorbenko et al., "The Role of Lipid-Protein Interactions in Amyloid-Type Protein Fibril Formation", Chemistry and Physics of Lipids, vol. 141, Nos. 1-2, Jun. 2006, pp. 72-82.

Okada et al., "Formation of Toxic Aβ(1-40) Fibrils on GM1 Ganglioside-Containing Membranes Mimicking Lipid Rafts: Polymorphisms in A(1-40) Fibrils", Journal of Molecular Biology, vol. 382, No. 4, Oct. 2008, pp. 1066-1074.

Ordonez-Gutierrez et al., "Repeated Intraperitoneal Injections of Liposomes Containing Phosphatidic Acid and Cardiolipin Reduce Amyloid-β Levels in APP/PS1 Transgenic Mice", Nanomedicine: Nanotechnology, Biology and Medicine, 2015, vol. 11, pp. 421-430.

* cited by examiner

LIPOSOMES CAPABLE OF EFFECTIVELY BINDING THE BETA AMYLOID PEPTIDE

FIELD OF THE INVENTION

The present invention relates to the field of the treatment, prevention and diagnosis of diseases associated with the presence in the body of large quantities of beta amyloid peptide.

BACKGROUND OF THE INVENTION

Alzheimer's disease is a neurodegenerative disorder characterised by progressive loss of memory and cognitive functions. It may be classified as dementia and its occurrence is such that it is the fourth most common cause of death in the industrialised nations, quite apart from the incalculable economic and social damage it causes.

In terms of anatomy and pathology, post-mortem examination of the brain tissue of an Alzheimer's patient reveals the presence of senile plaques and neurofibrillary tangles in the limbic system and the cortex. The plaques, which are located extracellularly, contain amyloid β (Aβ) peptide as their primary component, this peptide arising from amyloid precursor protein (APP) via a series of cleavages by proteolytic enzymes. Aβ peptide is produced in considerable quantities only in the brain of Alzheimer's patients and not of healthy people. The peptide, which has a relatively low molecular weight (approx. 4500 Da) and is produced in monomer form, tends to combine by means of weak interactions with other Aβ molecules, forming ever larger aggregations: oligomers, fibrils, plaques. While the monomer and oligomers are relatively soluble, fibrils and plaques are insoluble and are deposited in the brain in the form of amyloid aggregates which are then found the brain of Alzheimer's patients. These aggregates are toxic to neurons, causing them to degenerate so resulting in loss of cognitive abilities and death.

β Amyloid (Aβ) peptide, which is produced in abnormally large quantities in Alzheimer's disease, accumulates in the brain. It is assumed that a dynamic equilibrium exists: monomers⇌oligomers⇌fibrils⇌plaques. The existence of this equilibrium accounts for the increase in the quantity of insoluble aggregates in Alzheimer's brain: this is because the abnormal increase in monomer production in the disease shifts the equilibrium towards plaque formation.

β Amyloid peptide may also be found in the circulating blood, in equilibrium, through the blood-brain barrier, with that present in the brain. In confirmation of the existence of this latter equilibrium, papers published by other authors have shown that the administration of substances capable of binding Aβ peptide in the blood and removing it therefrom can also indirectly promote Aβ efflux from the central nervous system as well as amyloid plaque removal. This is known as "sink" effect. The most studied among these binding substances are antibodies injected into transgenic mice, used as a model of the disease. This is known as immunotherapy of Alzheimer's disease. The possibility of using other molecules capable of binding Aβ, such as for example the GM1 ganglioside lipid injected intravenously or the Nogo receptor injected subcutaneously, has also been tested with partial success.

If lipid molecules, or more generally molecules having amphipathic properties capable of promoting the "sink effect" when injected into the circulation, are to be used, they should be inserted into "vehicles" which are capable of enhancing their ability to interact with Aβ, while inhibiting their ability to interact with the immune system or the reticuloendothelial system which in contrast tends to eliminate these molecules from the circulation.

Liposomes are lipid vesicles made up of a double layer of amphipathic lipids enclosing an aqueous cavity. Liposome production is a simple, efficient and scalable method yielding a controlled product which is already used by the pharmaceutical industry for treating other human diseases. Moreover, using natural lipid molecules makes it possible to produce a biocompatible and biodegradable product. Liposomes have long been known as an excellent carrier system capable of incorporating both lipophilic or amphipathic molecules (in the double phospholipid layer) and hydrophilic molecules (in the internal aqueous core) and are widely used for the targeted transport of drugs and contrast agents to tissues of interest. Drug release, in vivo stability and biodistribution are determined by the size, surface charge, surface hydrophobicity and fluidity of the particle membrane. It is furthermore possible to prevent rapid uptake by the reticuloendothelial system by formulating them on the basis of natural lipid components. One feature of liposomes is the highly specific nature of the interaction between the type of lipid substrate used and the active substance to be transported. It has in fact been found that lipids with a high affinity towards one particular type of molecule are completely ineffective in binding other molecules. At the same time, even slight variations in the composition of the liposomes may greatly modify their level of activity towards the species to be bound (target). Furthermore, in the event that the target species is in equilibrium with other non-target species, an effectively working liposome must exhibit exclusive affinity towards the former species; in particular, in case of the monomer⇌oligomer⇌fibril⇌plaque equilibrium, it is important for the liposomes to have high affinity towards the "monomer" and "oligomer" component; a liposome with generalised affinity towards the various species would not significantly shift the equilibrium, while a liposome with a preferential affinity towards the higher species (fibrils, plaques) could shift the equilibrium in unwanted manner towards the formation of the species with greater pathogenic potential.

Although some examples of "sink effect" have been described experimentally, there is still no effective and reliable system available for binding beta amyloid peptide; moreover, no system is available which can readily be administered systemically; it is finally necessary to combine the above-stated effectiveness with a simple and low-cost production method which does not involve using costly synthetic and semisynthetic substances, and/or substances affecting the immune system of the patient.

SUMMARY OF THE INVENTION

Novel liposomes have now been identified which are capable of effectively binding beta amyloid peptide in "monomer" and "oligomer" form and which can be used for implementing the "sink effect" in ideal manner for treating Alzheimer's disease and any other disease associated with an abnormal increase in this peptide in the body. Binding ability is ensured by the presence in their formulation of specific natural lipids which have been identified by the Applicant. These comprise a constant component, made up of cholesterol and sphingomyelin, and an additional variable component, made up of some selected lipids.

The specific lipids capable of binding Aβ and the ability of liposomes containing these specific lipids to efficiently bind Aβ peptide were discovered in the course of research carried out by the inventors.

DETAILED DESCRIPTION

Figure 1:
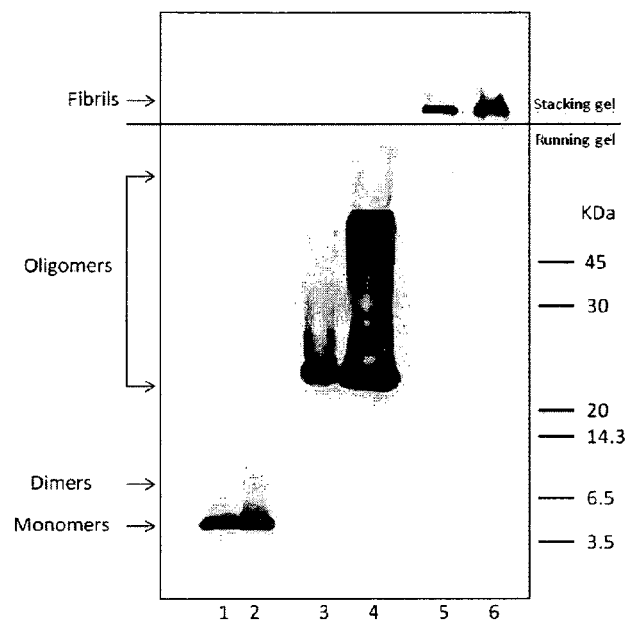
FIG. 1: Mono-dimensional electrophoresis under non-denaturing conditions of Aβ peptide (Aβ 1-42) in various states of aggregation, indicated by the arrows (monomers, oligomers and fibrils). Staining with Ab 6E10 anti-Aβ 1-42.

Liposomes composed of cholesterol, and sphingomyelin in a 1:1 molar ratio are known to exhibit high stability in circulation and to prevent rapid uptake by the reticuloendothelial system; however, as noted here by the Applicant, they exhibit an unsatisfactory ability to bind beta amyloid peptide.

The Applicant has now identified some selected lipids which, when formulated together with cholesterol:sphingomyelin 1:1, yield liposomes having a high to very high binding capacity towards Aβ peptide. The additional lipids useful for this purpose are selected from among cardiolipin, L-β,γ-dimyristoyl phosphatidic acid, dipalmitoyl L-α-phosphatidyl-DL-glycerol, and derivatives thereof. The additional lipid preferably amounts to a molar percentage of between 5 and 40%, more preferably from 15% to 25%, for example 20%, relative to the total number of moles of cholesterol, sphingomyelin and additional lipid; unlike the other above-stated lipids, having a standard molecular weight, sphingomyelin is known to occur in different forms with variations in molecular weight: however, in the present invention, any sphingomyelin may be used in the above-stated ratios, without significant variations in binding ability with Aβ peptide.

The liposomes may be prepared by means of per se known methods, as described for example in *Remington's Pharm. Sciences*, 21st ed., p. 314. All these processes, applied to preparing the above-stated liposomes, are part of the present invention. One preferred method is the preparation by extrusion: the preselected lipids are mixed in an organic solvent; the solvent is then removed yielding a lipid film; the film is resuspended in a physiological buffer and extruded under pressure through filters with pores of controlled diameter.

The resulting liposomes exhibit a high capacity of binding Aβ peptide, and in particular its monomeric and oligomeric component. As stated above, such binding is of considerable interest in the therapeutic and preventive treatment of diseases associated with the presence of abnormal quantities of Aβ peptide in the body, in particular Alzheimer's disease. The invention also provides the use of the liposomes here described in the prevention and treatment of diseases associated with abnormal production of Aβ peptide, as well as appropriate pharmaceutical compositions comprising said liposomes. Any pharmaceutical forms suitable for administering liposomes may be used for the purposes of the present invention; reference is in particular made to injectable solutions, for example by intravenous or intramuscular route, and infusions. The present compositions do not need to be administered directly into the brain, although this route of administration is an integral part of the present invention. In fact, the above-stated effects are also advantageously achieved by systemic administration: by sequestering beta amyloid peptide from the circulating blood, the liposomes bring about a concentration gradient such as to shift the monomer⇌oligomer⇌fibril⇌plaque equilibrium to the left in the cerebral compartment, so promoting plaque dissolution and inhibiting the formation of new plaques.

The liposomes formulated in this manner may contain further conventional ingredients commonly used in liposome formulations: examples of such ingredients are liposome-stabilising molecules, such as polyethylene glycol, which promote an extended circulation half-life of such preparations. The liposomes may also be loaded, at least in part, with drugs useful in the treatment of Alzheimer's disease. The resulting composition thus synergistically exploits two aspects of the liposomal component: on the one hand, the sequestering effect is used to reduce the presence of pathogenic species, on the other hand, the liposome's ability to act as a drug carrier, useful for transporting the drug to its site of action and preventing premature metabolisation are exploited.

Apart from therapeutic use, the liposomes of the invention may be used as biological reagents for in vitro applications, on cell cultures, etc., still for the purpose of binding and concentrating beta amyloid peptide.

One particularly useful field of application is diagnostics: thanks to their ability to sequester beta amyloid peptide, the liposomes may be incubated with a biological sample suspected to contain said peptide; after appropriate recovery from the sample, the liposomes are then broken down and the peptide is quantified according to known methods. The high affinity of the liposomes towards beta amyloid peptide makes it possible to concentrate small quantities of said peptide, which cannot be measured in the natural state, so making them quantifiable. Recovering specific quantities of peptide makes it possible to diagnose Alzheimer's disease, to quantify its severity or to detect a predisposition to it. This application is of considerable interest because no test is currently available which is capable of diagnosing Alzheimer's disease with certainty, diagnosis instead being made on the basis of probability by excluding other causes of dementia; it is thus of great interest to use the new liposomes here described which are capable of binding Aβ as a detector of amyloid plaques in a diagnostic context.

Inserting the lipids we have discovered and producing liposomes incorporating such lipids is a technically straightforward procedure which gives rise to a low-cost pharmaceutical product, easy and quick to prepare and potentially usable in vivo in humans for treating Alzheimer's disease via exploitation of the "sink effect". From this standpoint, it is a huge step forward in comparison with immunotherapy of the disease which involves using anti-Aβ antibodies or using GM1 ganglioside, production of which is complex and costly. Furthermore, said molecules may involve risks associated with immune response.

The product provided by the patent has great potential for treating Alzheimer's disease as an alternative to current palliative treatments. Alzheimer's disease accounts for 70% of progressive dementia in adults and, in the advanced stages of the disorder, patients suffering from Alzheimer's disease become incapable of carrying out any independent activity, living in a state of complete dependency on family members or healthcare staff. Seeking out an effective cure for this disease, which is capable of removing amyloid plaques present in the brain of patients, is thus of considerable medical interest.

EXPERIMENTAL SECTION

1. Preparation of Liposomes.

The liposomes, composed of cholesterol/sphingomyelin/ additional lipid in a 2/2/1 molar ratio, were prepared by extrusion method. 1.3 μmol of total lipids were mixed in organic solvent (chloroform/methanol 2:1, vol:vol), which was subsequently removed under a gentle stream of nitrogen, followed by a vacuum pump for at least 3 hours. The resulting lipid film was resuspended in physiological buffer (10 mM tris-HCl, 150 mM NaCl, 1 mM EDTA pH 7.4) and extruded 10 times under pressure (20 bar) through polycarbonate filters with pores of 100 nm diameter using an extruder (Lipex Biomembranes).

2. Composition of Liposomes.

The liposomes are composed of a constant portion based on cholesterol/sphingomyelin (in 1:1 molar ratio; sphingomyelin from egg yolk, MW: 703.04) and a variable portion, likewise composed of a lipid. The lipids were mixed in the following molar ratio: cholesterol/sphingomyelin/variable lipid, 40/40/20. Liposomes were furthermore prepared by changing the contribution of the variable portion, i.e. by using between 5 and 40 mol % of the variable lipid and adjusting the amount of the constant portion (30/30/40 and 47.5/47.5/5).

3. Aβ Peptide.

The peptide was sourced commercially (Sigma) and is the human form of beta amyloid peptide, in particular it is the 1-42 fragment, namely the main component of the amyloid plaques found in the brain of Alzheimer's patients. The freeze-dried peptide is resuspended in a special solvent (hexafluoroisopropanol HFIP, Sigma) capable of breaking down any aggregates present in the preparation.

The solvent is then removed under a gentle stream of nitrogen, followed by a vacuum pump for at least 3 hours. This ensures that the peptide is present in monomeric form. The dried peptide is then directly resuspended with the extruded liposomes and incubated with them as described below. The experiments investigating the interaction of the peptide with the liposomes are then carried out using the peptide in various states of aggregation: oligomeric and fibrillary, following the protocols described in the literature. Control experiments, such as native electrophoresis under non-denaturing conditions and atomic force microscopy (AFM), obviously make it possible to check the state of aggregation of the peptide.

4. Binding Procedure.

The liposomes prepared in this manner were tested for their ability to interact with and bind Aβ peptide using discontinuous density gradient ultracentrifugation to separate the bound peptide from the peptide which is not bound to the liposomes. The liposomes (1.3 μmol of lipids) were incubated with the Aβ 1-42 peptide (1.0 μg) for 90 minutes at 37° C. and then ultracentrifuged. The gradient was prepared by layering in the bottom of a test tube 1350 μL of 80% sucrose dissolved in buffer, 450 μL of sample (liposomes and peptide after incubation), 1350 μL of 50% sucrose dissolved in buffer and 1350 μL of buffer.

After centrifugation at 140,000 g for 2 hours a 4° C., 10 fractions of 450 μL each were collected and consolidated in 2 pools: the first 5 fractions being taken as representative of the protein associated with the liposomes and the final 5 as representative of the unbound protein. The quantity of Aβ peptide was then determined by ELISA assay. All the binding experiments were repeated at least three times.

5. Results 5.1 State of Aggregation of Aβ Peptide

The monomeric form of the peptide was obtained by resuspending the freeze-dried peptide in a polar solvent (HFIP); the oligomeric form was obtained by resuspending the peptide in the above-described physiological buffer supplemented with dimethyl sulfoxide (DMSO) and incubating for 24 hours at 4° C.; the fibrillary form was obtained by resuspending the peptide in an acidic solution or directly in deionised water. The state of aggregation of the various preparations was checked by non-denaturing electrophoresis and AFM. FIG. 1 shows an electrophoresis run under native conditions for Aβ peptide in monomeric, oligomeric and fibrillary form indicated by the arrows. The polyacrylamide gel was transferred onto a nitrocellulose membrane by Western blotting. Protein bands were detected by immunodecoration with a specific antibody directed against AR and a secondary antibody capable of recognising the primary antibody, conjugated to the peroxidase enzyme.

Signal detection by Chemioluminescence.

Figure 2:
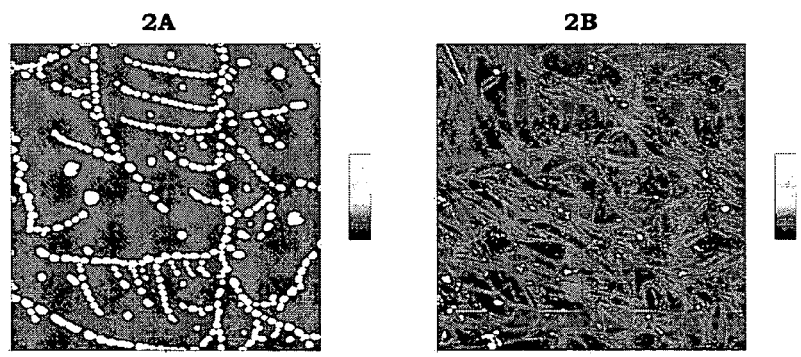
FIG. 2: Images of Aβ peptide, obtained by atomic force microscopy, in various states of aggregation: oligomeric and fibrillary. 2A: oligomers; 2B: fibrils. Image size: 10 μm×10 μm.

FIG. 2, in contrast, shows images representative of Aβ chemioluminescence in oligomeric and fibrillary form obtained by AFM.

5.2 Binding Experiments Between Liposomes and Aβ

Figure 3:
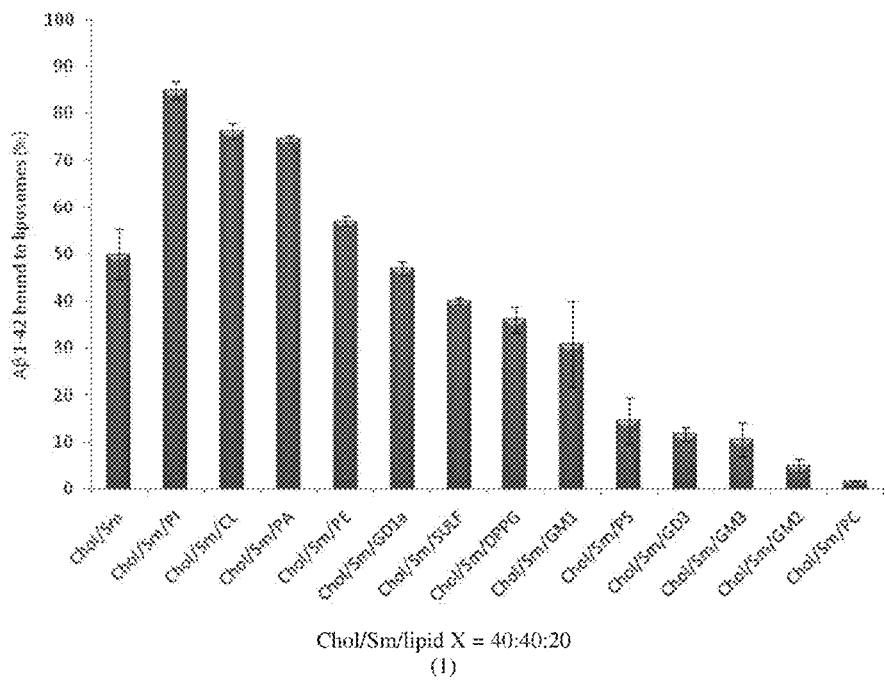
FIG. 3: Histogram 1 shows the results of binding experiments of liposomes with Aβ: percentages of Aβ protein bound by liposomes.
Figure 4:
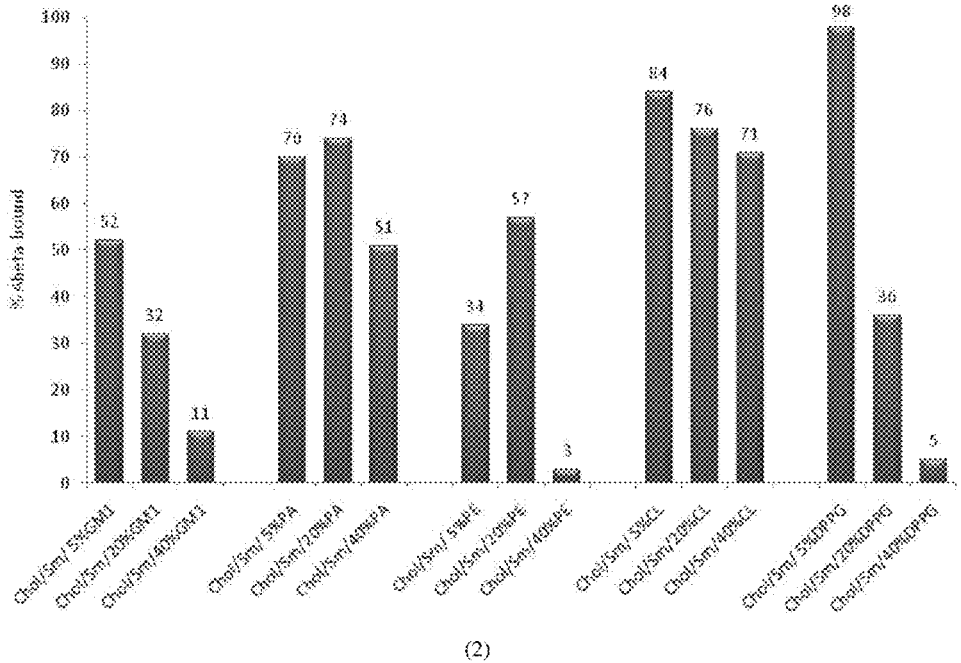
FIG. 4: Histogram 2 compares the percentages of Aβ protein bound by liposomes containing different percentages of variable lipid.

The results relating to the study of interaction between liposomes and Aβ peptide are shown in the histograms illustrated in FIGS. 3 and 4. The histograms show the proportion of peptide bound to liposomes of differing lipid composition, determined by density gradient ultracentrifugation experiments followed by quantification of the peptide by ELISA assay.

In particular, histogram 1 (FIG. 3) shows the percentages of Aβ protein bound by liposomes in which the lipids: cholesterol/sphingomyelin/variable lipid, are present in a 40/40/20 molar ratio.

Histogram 2 (FIG. 4), in contrast, compares the percentages of Aβ protein bound by liposomes containing different percentages of variable lipid, within the above-stated range of 5-40 mol %, relative to the total of the three lipids present.

The abbreviations of the lipids shown on the x axis of the histograms correspond to the following chemical names:

Chol=cholesterol; Sm=sphingomyelin; PI=phosphatidylinositol; CL=cardiolipin; PA=L-β,γ-dimyristoyl-α-phosphatidic acid; PE=phosphatidylethanolamine; PG=phosphatidylglycerol; GM1=monosialylated GM1 ganglioside; GD1a=disialylated GD1a ganglioside; SULF=sulphatides; GM3=monosialylated GM3 ganglioside; GD3=disialylated GD3 ganglioside; PS=phosphatidylserine; GM2=monosialylated GM2 ganglioside; DPPG=dipalmitoyl L-α-phosphatidyl-DL-glycerol.

As can be seen from FIGS. 3 and 4 (histograms 1 and 2), at an identical molar percentage of variable lipid, the binding capacity for Aβ protein varies greatly among the various lipids taken into consideration (histogram 1); however, tests performed with different molar percentages of the same lipid (histogram 2), yielded results which were completely unpredictable on the basis of the values obtained with the 40:40:20 ratio of histogram 1.

It is interesting to note that the better results, always in comparison with the liposomes composed solely of cholesterol and sphingomyelin, are obtained with liposomes containing 5% DPPG, 5% CL and 20% PA.

Liposomes of nanometric dimensions (diameter 100 nm) having a different lipid composition were prepared by extrusion procedure, and their ability to bind Aβ 1-42 peptides was investigated.

The liposomes were made up of a matrix of cholesterol/sphingomyelin (Chol/Sm molar ratio 1:1) supplemented with a molar percentage of 5, 20 or 40% of L-β,γ-dimyristoylphosphatidic acid or derivatives thereof, in particular cardiolipin or dipalmitoyl L-α-phosphatidyl-DL-glycerol (anionic phospholipids). The dimensions of the liposomes, the z potentials and the polydispersion index were determined by Dynamic Laser light Scattering (DLS).

The affinity of the liposomes towards Aβ peptide in the different forms of aggregation (monomers, oligomers and fibrils) which may be found in the brains of Alzheimer's disease patients was determined by Surface Plasmon Resonance (SPR), ultracentrifugation on a discontinuous sucrose density gradient and fluorescence quenching of fluorescent Aβ.

These preliminary studies have shown that liposomes made up of Chol/Sm/anionic phospholipids exhibited a strong ability to bind Aβ peptide relative to Chol/Sm alone, Chol/Sm/zwitterionic phospholipids or Chol/Sm/sphingolipids. In particular, liposomes containing anionic phospholipids exhibited affinity constant (Kd) values in the nanomolar range (100-200 nM) for all the Aβ aggregates investigated. Affinity appears to follow the decreasing order: fibrils>oligomers>monomers.

The high affinity of the liposomes for Aβ peptide may be exploited for binding Aβ cerebral aggregates (diagnostic applications) and, possibly, for removing/sequestering them from the brains of patients (therapeutic applications).

These nanoparticles may readily be prepared and functionalised with contrast agents for diagnostic purposes or with molecules capable of disaggregating and/or preventing the aggregation of Aβ peptides. The inventors are carrying out experiments to this end to investigate the effect of the above-stated liposomes on the aggregation/disaggregation of Aβ by atomic force microscopy (AFM), thioflavin T (ThT) assay and electrophoresis methods. Preliminary results show that the liposomes containing in particular cardiolipin and L-β,γ-dimyristoylphosphatidic acid are capable of inhibiting the formation of fibrils from the monomeric preparation of Aβ peptide.

The invention claimed is:

1. A method of reducing Aβ peptide in a patient affected by Alzheimer's disease, characterized by administering to said patient by injection and/or infusion of an amount of liposomes sufficient to reduce Aβ peptide in said patient, wherein the liposomes comprise cholesterol and sphyngomyelin in a 1:1 molar ratio, and one or more additional lipids selected from among cardiolipin and/or L-β,γ-dimyristoyl phosphatidic acid, and wherein the additional lipid accounts for a molar percentage of from 5 to 20%, relative to the total content of cholesterol, sphingomyelin and additional lipid.

2. The method of claim 1, wherein the liposomes are administered via an injectable pharmaceutical composition.

3. The method of claim 2, wherein the injectable pharmaceutical composition is a solution, suspension or emulsion.

4. The method of claim 3, wherein the pharmaceutical composition is injected into a body compartment different from the brain.

5. The method of claim 4, wherein the injectable pharmaceutical composition is injected systemically, in particular intravenously or intramuscularly.

6. The method of claim 1, wherein the liposomes inhibit the aggregation of Aβ peptide from monomers to plaques.

7. The method of claim 1, wherein the liposomes inhibit aggregation of Aβ peptide from monomers to plaques in the brain.

8. The method of claim 1, wherein the additional lipid accounts for a molar percentage of 5%, relative to the total of cholesterol, sphingomyelin and additional lipid.

9. The method of claim 1, wherein the additional lipid accounts for 15 to 20% mol %, relative to the total of cholesterol, sphingomyelin and additional lipid.

10. The method of claim 1, wherein the additional lipid accounts for 20 mol %, relative to the total of cholesterol, sphingomyelin and additional lipid.

11. The method of claim 1, wherein the liposomes selectively bind fibrils in the patient.

12. A method of reducing Aβ peptide in a patient affected by an overproduction of Aβ peptide, characterized by systemically administering to said patient by injection and/or infusion of an amount of liposomes sufficient to reduce Aβ peptide in said patient, wherein the liposomes comprise cholesterol and sphyngomyelin in a 1:1 molar ratio, and one or more additional lipids selected from among cardiolipin and/or L-β,γ-dimyristoyl phosphatidic acid, and wherein the additional lipid accounts for a molar percentage of from 5 to 20%, relative to the total content of cholesterol, sphingomyelin and additional lipid.

* * * * *